(12) United States Patent
Sarstedt

(10) Patent No.: US 7,951,090 B2
(45) Date of Patent: May 31, 2011

(54) CANNULA EQUIPPED WITH A PROTECTIVE HOUSING

(75) Inventor: Walter Sarstedt, Nümbrecht (DE)

(73) Assignee: Sarstedt AG & Co, Nuembrecht (DE)

( * ) Notice: Subject to any disclaimer, the term of this patent is extended or adjusted under 35 U.S.C. 154(b) by 82 days.

(21) Appl. No.: 12/293,829

(22) PCT Filed: Mar. 16, 2007

(86) PCT No.: PCT/DE2007/000502
§ 371 (c)(1),
(2), (4) Date: Mar. 11, 2009

(87) PCT Pub. No.: WO2007/110043
PCT Pub. Date: Oct. 4, 2007

(65) Prior Publication Data
US 2010/0234767 A1 Sep. 16, 2010

(30) Foreign Application Priority Data
Mar. 21, 2006 (DE) .......................... 10 2006 013 322

(51) Int. Cl.
*A61B 5/00* (2006.01)
*A61M 5/00* (2006.01)
*A61M 5/32* (2006.01)
*B65D 81/00* (2006.01)

(52) U.S. Cl. ......................... 600/573; 604/110; 604/192

(58) Field of Classification Search ................... 600/573, 600/583; 604/187, 192, 198, 110
See application file for complete search history.

(56) References Cited

U.S. PATENT DOCUMENTS

| 3,658,061 | A | 4/1972 | Hall |
| 5,017,189 | A | 5/1991 | Boumendil ................... 604/192 |
| 5,139,489 | A | 8/1992 | Hollister |
| 5,154,285 | A | 10/1992 | Hollister |
| 5,490,841 | A | 2/1996 | Landis |
| 5,632,732 | A * | 5/1997 | Szabo et al. .................. 604/192 |
| 2002/0156424 | A1 | 10/2002 | Suzuki .......................... 604/192 |

FOREIGN PATENT DOCUMENTS

| DE | 69127906 U | 2/1998 |
| DE | 69225609 U | 9/1998 |
| EP | 1186313 | 3/2002 |
| EP | 1602327 | 12/2005 |

* cited by examiner

*Primary Examiner* — Max Hindenburg
*Assistant Examiner* — Jonathan M Foreman
(74) *Attorney, Agent, or Firm* — Andrew Wilford

(57) ABSTRACT

The invention relates to a cannula, preferably equipped with a cannula holder for, in particular a blood sampling device, which comprises a pivotable protective housing (102) for a free end of the cannula. Said protective housing (102) is closed on the periphery except for a cannula insertion opening (8) provided between opposing side walls. Said insertion opening is produced by at least one pair of lamella (8a, 8b), formed on the side walls, the lamella tapering towards one another in the manner of a funnel and forming an expandable funnel slot. The protective housing (102) comprises two housing parts which can be inserted into each other. The inner housing (2a) comprises the pair of lamella (8a, 8b) and an outer housing (11), which surrounds the inner housing (2a), is embodied as a sleeve that is less elastic than the inner housing (2a).

3 Claims, 2 Drawing Sheets

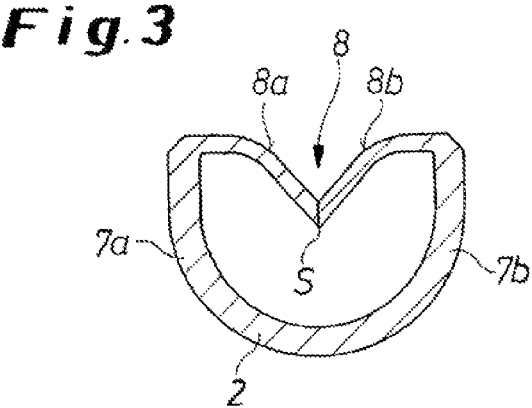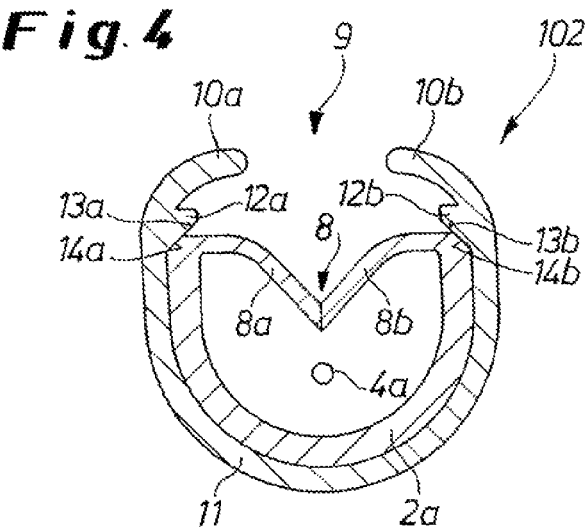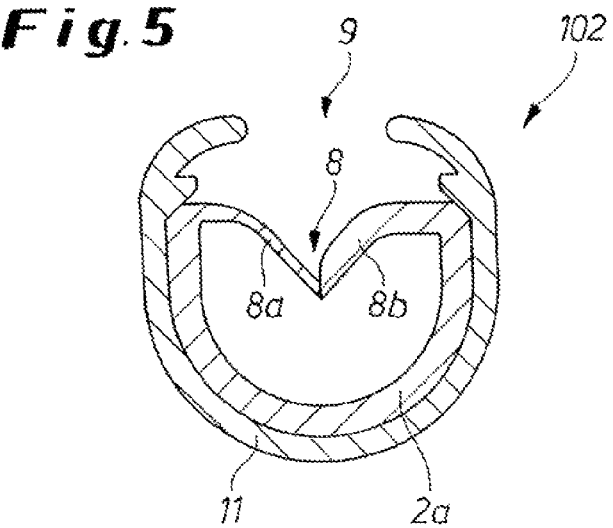

CANNULA EQUIPPED WITH A PROTECTIVE HOUSING

CROSS REFERENCE TO RELATED APPLICATIONS

This application is the US national phase of PCT application PCT/DE2007/000502, filed 16 Mar. 2007, published 4 Oct. 2007 as WO 2007/110043, and claiming the priority of German patent application 102006013322.6 itself filed 21 Mar. 2006, whose entire disclosures are herewith incorporated by reference.

FIELD OF THE INVENTION

The invention relates to a cannula, preferably equipped with a cannula holder for, in particular, a blood-sampling device, and provided with a pivotal protective casing for a free end of the cannula. The protective casing is laterally closed except for a cannula insertion slot provided between opposing side walls. The insertion slot is defined between at least one pair of lips formed on the side walls, the lips angled toward one another like a funnel and forming a widenable funnel slot.

BACKGROUND OF THE INVENTION

Such a blood-sampling device equipped with a safety or protective casing made in a plurality of variations is known from U.S. Pat. No. 5,490,841, DE 691 27 906 T2 (U.S. Pat. No. 5,139,489), DE 692 25 609 (U.S. Pat. No. 5,154,285), and U.S. Pat. No. 3,658,061. Such protective casings are also used for cannulas of injection syringes. In order for the user or a third party to not contact the cannula or any blood drops remaining thereon and also to avoid needle sticks, the protective casing is pivoted flush toward the cannula after completion of blood sampling, which is then received in the protective casing. The protective casing has an elongated, opening as the cannula insertion slot. The cannula enters into this slot once the elongated protective casing is pivoted to fit flush with the cannula.

Retaining means are provided in the protective casing itself to prevent the enclosed cannula from coming out of the protective casing on its own. These retaining means are formed as hooks provided in the compartment surrounded by the protective casing walls, and thus inside the protective casing on the base wall, or in the region of the base, thereof. In these blood-sampling devices the protective casing is mounted via a tab and a retaining ring, either in rigid or pivoting manner on the cannula holder.

The known protective casings have the disadvantage that the retaining hooks cannot safely prevent the cannula from coming is out on its own. It is not impossible for the cannula to slide out laterally from the protective casing along with the free hook ends. This is substantially facilitated, such as described in U.S. Pat. No. 5,490,841, by the fact that the insertion slot opens wider when pressure is applied from the slot side onto the lip extending largely across the entire casing length, which are flexible to ease insertion of the cannula, such that the cannula insertion slot is widened and forced apart. The cannula/needle can then exit unintentionally from the protective casing without any problem. This creates therefore the additional problem that sometimes even contaminated fluid may exit. Aside from this a protective casing equipped with additional retaining means or hooks can only be produced at additional expense and additional holes through the casing (compare to above-mentioned DE 691 27 906 and DE 962 25 609). Finally, the practically required threading of the free cannula end into the hooks requires a certain degree of skill, and particular close attention on the part of the user.

OBJECT OF THE INVENTION

The object of the invention is to provide a standard cannula free of these disadvantages, and to provide it with a high safety function for the user.

SUMMARY OF THE INVENTION

This object is attained according to the invention in that the protective casing is comprised of inner and outer casing parts that are connected with each other, the inner casing part comprising the pair of lips and the outer casing part enclosing the inner casing part being embodied as a less elastic sleeve than the inner casing part. The invention therefore departs from the described, common one-piece construction of a protective casing, and makes it possible for the inner casing part to consist of elastic, flexible material to form the flexible pair of lips, although alternatively only one lip would need to be flexible, while the other lip can be rigid to protect from compressive forces applied from the outside due to the more massive, substantially inelastic outer casing part such that the funnel slot is no longer able to undesirably widen. For this purpose it does not matter whether the inner casing part is connected to the cannula holder, or not, and furthermore, whether the less elastic outer casing part is slid on, or the outer casing part is connected to the cannula holder, and the inner casing part is then inserted into it.

Another embodiment attains the object of the invention in that the protective casing is comprised of inner and outer casing parts that are inserted into each other, the inner casing part having a pair of lips and the outer casing part enclosing the inner casing part being formed as a less elastic sleeve than the inner casing part, the outer casing part further being equipped with contact surfaces that are advantageously formed as angled flat or round surfaces to exert an inward locking force toward funnel slot upon exterior pressure onto opposite, optionally provided surfaces of the inner casing part.

For this reason it is recommended that the outer casing part exerting the compressive force or transferring an unintentional outer pressure be formed with angular faces or similar contact surfaces and means enabling a targeted initiation of force at that location at which it overlaps the inner casing part on top, at free ends of the side walls from which the lips is extend and that face each other to abut optional angular faces or similar contact surfaces. The surface contact thus achieved contributes to the defined initiation of force there, namely in the region of and on top of the lips. The lateral compressive force exerted across the outer casing part keeps the funnel slot safely closed, i.e. free ends of the flexible lips confronting each other continuously abut each other.

Furthermore, an outer access opening is provided outside the inner cannula insertion slot of the inner casing part shaped like a funnel by means of the surrounding outer casing part, the outer access opening being formed by outer casing part outer edge ridges protruding over the side walls of the inner casing part and projecting toward each other. Any contact with the inner casing part, particularly with the lips, is excluded such that the safety function cannot be adversely affected. The access opening does not allow, for example, a finger of a user to pass the outer casing part outer edge ridges and press on the lips.

BRIEF DESCRIPTION OF THE DRAWING

Additional characteristics and details of the invention are obvious from the claims and the following description of the illustrated embodiments of the invention illustrated in the drawings in connection with a blood-sampling device. Therein:

FIG. 3 is a cross-section through the protective casing as a detail of FIG. 1;

FIG. 4 is a large-scale cross-sectional of the protective casing at an enlarged scale as a detail of FIG. 2; and FIG. 5 shows a variation of the protective casing illustrated in FIG. 4.

SPECIFIC DESCRIPTION

Figure 1:
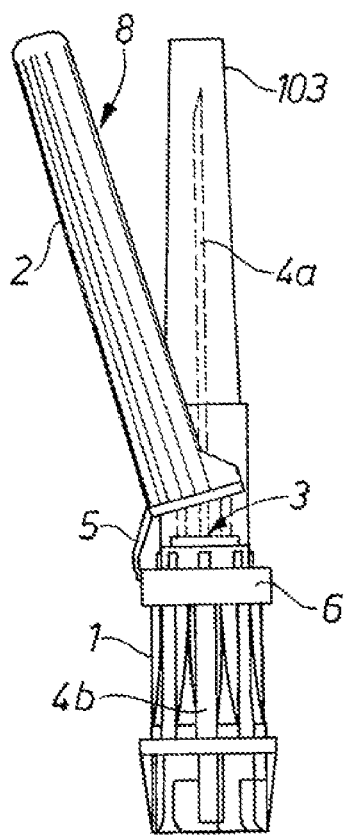
FIG. 1 is an overall view of a cannula holder as a detail of a blood-sampling device and provided with a standard prior-art casing, shown before closing.
Figure 2:
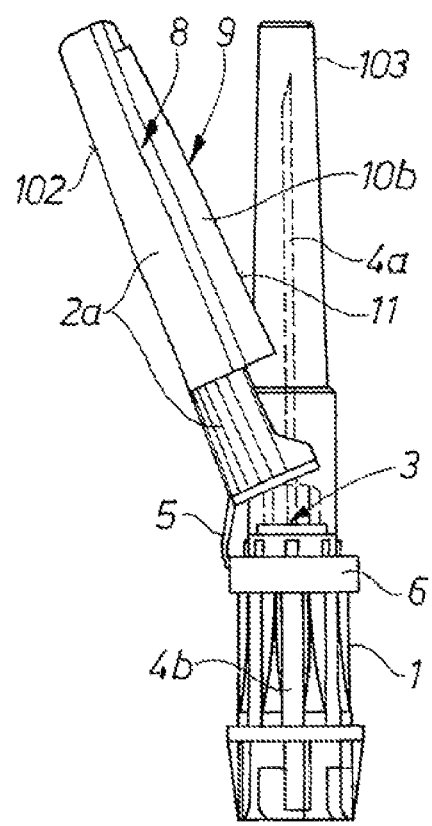
FIG. 2 is an overall view of a cannula holder as a detail of a blood-sampling device and provided with a protective casing comprised of two parts, shown before closing.

A cannula holder 1 shown in FIGS. 1 and 2 that can be connected to a blood-sampling tube (not illustrated) is usually supplied with a pivoted- or folded-in protective casing 2 or 102, a free cannula end 4a of the cannula or the of double cannula 3 in this case being protected by means of a separate casing 103 that is removed before use. After use the free cannula end 4a of the double cannula 3 is surrounded by the protective casing 2, or 102, and enclosed by same.

The known protective casing 2 made of a flexible plastic by means of injection molding has a cannula insertion slot 8 formed by a flexible pair of lip elements 8a and 8b—hereinafter referred to as lips—that are formed on the free ends of the side walls 7a and 7b thereof, tapering toward one another like a funnel and extending in the illustrated embodiment substantially across the entire longitudinal length of the casing. The flexible lips 8a and 8b form a mouth or funnel slot S, as shown in FIG. 3. A cannula trapped inside the protective casing 2 can therefore undesirably slide back out of the protective casing via the funnel slot S and the cannula insertion slot 8, if an unintentional compressive force is exerted on the lips.

This disadvantage of the undesired coming-out of the free cannula end 4a is avoided according to FIGS. 2 and 4 by means of a two-part embodiment of the protective casing 102. It consists of an elastic inner casing part 2a having the flexible lips 8a and 8b, and an outer casing part 11 fitted over same but made of a more dimensionally stable, less elastic material than that of the inner casing part 2a. In the shown embodiment the inner casing part 2a is connected to a retaining ring 6 of the cannula holder 1 via a strip or tab hinge 5; alternatively the outer casing part 11 can be connected to the retaining ring 6 and the elastic inner casing part 2a can then be slid into the outer casing part. In any case the outer casing part 11 protects the flexible inner casing part 2a from any unintentional outer compressive forces exerted, and keeps the funnel slot S closed so it cannot be opened.

The outer casing part 11 is made such that an access opening 9 is formed outward of a funnel-shaped cannula-insertion slot 8 of the inner casing part 2a. It is formed by outer casing part edge ridges 10a and 10b that project over the lips 8a and 8b of the inner casing part 2a, or over the side walls 7a and 7b, thereof, toward each other and that are formed with their outer edges confronting each other. In the shown embodiment inner ridge formations 12a and 12b having angled face 13a and 13b, or alternatively curved inner faces, are provided at the base of the outer casing part outer edge ridges 10a and 10b and abut complementary angled faces 14a and 14b at the free ends of the side walls 7a and 7b of the inner casing part 2a. A compressive force acting upon the outer casing part 11 is created in the flexible lips 8a and 8b in a defined manner by these annular faces 13a and 13b, and 14a and 14b, and/or by the side walls 7a and 7b. Opening of the funnel slot S is thereby avoided. Furthermore, the surfaces 13a and 13b, and 14a and 14b provide a guide during sliding of the outer and inner casings 11 or 2a into each other for concentric assembly of the same. This also applies in the case of the embodiment of the protective casing 102 shown in FIG. 5, which differs from the configuration described above only in that only one lip 8a is flexible, while the other lip 8b of the nonetheless unchanged overall flexible pair of lips is configured in a rigid manner.

The invention claimed is:

1. A cannula equipped with a cannula holder for a blood-sampling device and comprising a pivotal protective casing for a free end of the cannula, the protective casing being laterally closed except for a cannula insertion slot provided between opposing side walls, the insertion slot being formed by at least one pair of lips formed on the side walls and angled toward each other like an outwardly flaring funnel and forming a widenable funnel slot, wherein the protective casing comprises inner and outer casing parts concentrically inserted into each other, the inner casing part comprises the pair of lips, and the outer casing part surrounds the inner casing part, is formed as a sleeve that is less elastic than the inner casing part, and presses inward on the inner casing part to bias the lips into engagement with each other and thereby bias the slot closed.

2. A cannula equipped with a cannula holder for a blood-sampling device and comprising a pivotal protective casing for a free end of the cannula, the protective casing being laterally closed except for a cannula insertion slot provided between opposing side walls, the insertion slot being formed by at least one pair of lips formed on the side walls and angled toward each other like a funnel and forming a widenable funnel slot, wherein the protective casing comprises inner and outer casing parts concentrically inserted into each other, the inner casing part comprising the pair of lips and the outer casing part, which surrounds the inner casing part, is formed as a sleeve that is less elastic than the inner casing part; and the outer casing part is equipped with contact surfaces that exert an inward locking force toward the funnel slot on opposing, complementarily provided contact surfaces of the inner casing part so as to urge the lips together and thereby bias the slot closed.

3. In combination with a cannula having a free end projecting along an axis from a holder base, a protective casing comprising:

a generally tubular inner part formed with a pair of axially extending lips having edges releasably engaging each other at an axially extending normally closed slot, at least one of the lips being elastically flexible and bearing angularly on the lip, the lips converging radially inward at the slot;

a generally tubular outer part that is substantially more rigid than the inner part, that generally coaxially surrounds the inner part, and that is formed with an axially extending outer slot aligned radially with the inner slot; and hinge means for supporting the inner and outer parts on the base for movement between an open position with the cannular free end outside of the inner and outer parts and available for use and a closed position generally coaxially surrounding the cannula free end and wholly enclosed inside the inner part, the one lip being sufficiently flexible that it deflects and lets the cannula free end pass through the inner slot on movement of the parts from the open to the closed position.

\* \* \* \* \*